US008430672B2

(12) United States Patent
Teicher et al.

(10) Patent No.: US 8,430,672 B2
(45) Date of Patent: Apr. 30, 2013

(54) METHOD FOR ASSESSING AUDITORY ATTENTION AND VIGILANCE

(75) Inventors: Martin H. Teicher, Rye, NH (US); Dennis M. Kim, Somerville, MA (US)

(73) Assignee: The McLean Hospital Corporation, Belmont, MA (US)

(*) Notice: Subject to any disclaimer, the term of this patent is extended or adjusted under 35 U.S.C. 154(b) by 1007 days.

(21) Appl. No.: 11/660,880

(22) PCT Filed: Aug. 24, 2005

(86) PCT No.: PCT/US2005/030083
§ 371 (c)(1),
(2), (4) Date: Apr. 8, 2009

(87) PCT Pub. No.: WO2006/023964
PCT Pub. Date: Mar. 2, 2006

(65) Prior Publication Data
US 2009/0202966 A1    Aug. 13, 2009

Related U.S. Application Data

(60) Provisional application No. 60/603,898, filed on Aug. 24, 2004.

(51) Int. Cl.
*G09B 19/04* (2006.01)
(52) U.S. Cl.
USPC ........................................................ 434/236
(58) Field of Classification Search ............... 434/236
See application file for complete search history.

(56) References Cited

U.S. PATENT DOCUMENTS

| | | | |
|---|---|---|---|
| 5,511,982 | A | 4/1996 | Pigache et al. |
| 5,868,683 | A | 2/1999 | Protopapas et al. |
| 5,911,581 | A * | 6/1999 | Reynolds et al. ............ 434/236 |
| 5,940,801 | A | 8/1999 | Brown |
| 6,053,739 | A | 4/2000 | Stewart et al. |
| 6,435,878 | B1 | 8/2002 | Reynolds et al. |
| 6,457,362 | B1 | 10/2002 | Wright et al. |
| 6,475,161 | B2 | 11/2002 | Teicher et al. |
| 6,554,439 | B1 | 4/2003 | Teicher et al. |
| 6,579,234 | B2 | 6/2003 | Lowen et al. |
| 6,685,652 | B1 | 2/2004 | Teicher et al. |
| 6,994,670 | B2 | 2/2006 | Teicher et al. |
| 2003/0233032 | A1 | 12/2003 | Teicher et al. |
| 2009/0005648 | A1 | 1/2009 | Teicher et al. |

FOREIGN PATENT DOCUMENTS

| | | |
|---|---|---|
| JP | A-H06-090934 | 5/1994 |
| JP | A-H11-150777 | 2/1999 |
| WO | WO 01/87142 | 11/2001 |
| WO | WO 2005/074801 | 8/2005 |
| WO | WO 2006/029021 | 3/2006 |

OTHER PUBLICATIONS

Masellis, M., "Evidence for Temporal Processing Deficits in Children with Attention Deficit Disorder and Language Impairments on a Dichotic Listening Task," Doctoral and Masters 1998 to 2002, National Library of Canada (1998).
English Translation of Notice of Reasons for Rejection, Issued Dec. 27, 2010.
Boer et al., "The Selective-Listening Task as a Test for Pilots and Air Traffic Controllers," *Mil. Psychol.* 9:137-149, 1997.
Forbes, G.B., "Clinical Utility of the Test of Variables of Attention (TOVA) in the Diagnosis of Attention-Deficit/Hyperactivity Disorder," *J. Clin. Psychol.* 54:461-476, 1998.
Gopher et al., "Individual Differences in Attention and the Prediction of Flight Criteria," *Percept. Mot. Skills* 33:1335-1342, 1971.
Greenberg, L.M., "An Objective Measure of Methylphenidate Response: Clinical Use of the MCA," *Psychopharmacol. Bull.* 23:279-282, 1987.
Halperin et al., "Specificity of Inattention, Impulsivity, and Hyperactivity to the Diagnosis of Attention-Deficit Hyperactivity Disorder," *J. Am. Acad. Child Adolesc. Psychiatry* 31:190-196, 1992.
Masellis, Maria C., "Evidence for Temporal Processing Deficits in Children with Attention Deficit Hyperactivity Disorder and Language Impairments on a Dichotic Listening Task," Thesis Dissertation, University of Toronto, 1998 (36 pages).
Rosvold et al., "A Continuous Performance Test of Brain Damage," *J. Consult. Clin. Psychol.* 20:343-350, 1956.
Sprague et al., "Methylphenidate in Hyperkinetic Children: Differences in Dose Effects on Learning and Social Behavior," *Science* 198:1274-1276, 1977.
Springer et al., "Dichotic Listening Failure in Dysphoric Neuropsychiatric Patients who Endorse Multiple Seizure-Like Symptoms," *J. Nerv. Ment. Dis.* 179:459-467, 1991.
Teicher et al., "Objective Measurement of Hyperactivity and Attentional Problems in ADHD," *J. Am. Acad. Child Adolesc. Psychiatry* 35:334-342, 1996.
Teicher et al., "Novel Strategy for the Analysis of CPT Data Provides New Insight into the Effects of Methylphenidate on Attentional States in Children with ADHD," *J. Child Adolesc. Psychopharmacol.* 14:219-232, 2004.
Tinius, Timothy P., "The Integrated Visual and Auditory Continuous Performance Test as a Neuropsychological Measure," *Arch. Clin. Neuropsychol.* 18:439-454, 2003.
Examiner's First Report in Australian Patent Application No. 2005277062, mailed Feb. 3, 2010.
Communication Issued in European Patent Application No. 05791178.6-2221, mailed Aug. 13, 2009.
Reply to Communication in European Patent Application No. 05791178.6-2221, mailed Sep. 10, 2010.
International Search Report for PCT/US2005/030083, completed Jan. 23, 2006, mailed Apr. 4, 2006.
International Preliminary Report on Patentability for PCT/US2005/030083, issued Feb. 28, 2007.
Written Opinion of the International Searching Authority for PCT/US2005/030083, completed Jan. 23, 2006, mailed Apr. 7, 2006.
Minami, Kenji Dichotic Listening Test in Preschool Children by a Dichotic Monitoring Task, Studies in Childhood Education of Kobe Shinwa Women's University, vol. 20:63-73, 2001. (English Abstract included).

* cited by examiner

*Primary Examiner* — Kesha Y. Frisby
(74) *Attorney, Agent, or Firm* — Clark & Elbing LLP

(57) ABSTRACT

Provided are methods for assessing the attentional state of a subject by scoring the subject's response to auditory stimuli. The methods can be used to diagnose psychological and behavioral disorders, such as attention deficit disorder or hyperkinetic disorder.

10 Claims, No Drawings

METHOD FOR ASSESSING AUDITORY ATTENTION AND VIGILANCE

CROSS-REFERENCE TO RELATED APPLICATIONS

This application is the U.S. National Stage of International Application No. PCT/US2005/030083, filed Aug. 24, 2005, which claims benefit of the U.S. Provisional Application No. 60/603,898, filed Aug. 24, 2004.

BACKGROUND OF THE INVENTION

The present invention relates to the auditory testing of individuals for an assessment of vigilance or for an attention deficit disorder.

It is common practice that a continuous performance test (CPT) form part of the physical examination for attention deficit disorders. The continuous performance attention test has been in use since the mid 50's (Rosvold et al., *J. of Consulting and Clinical Psychology* 20: 343-350, 1956), with computerized versions available in the 1970's (Greenberg, *Psychopharmacol. Bull.* 23: 279-282, 1987).

A diagnostic assessment of psychological conditions can be made by conducting a sequence of continuous performance tests where information is recorded to reflect the number of target stimuli correctly identified, the number of target stimuli missed, the number of responses to non-target stimuli, the number of non-target stimuli correctly missed, and the final interstimulus interval (U.S. Pat. No. 5,940,801). Improvements have been made to this method for evaluating attention deficit hyperactivity disorder (ADHD) in children by the incorporating an analysis of the test subject's movement patterns into the evaluation (see Teicher et al., *J. Am. Acad. Child Adolesc. Psychiatry* 35: 334-342, 1996). A version of such a testing system (the OPTAx™ test system) is now commercially available.

Auditory tests have also been employed for assessing an individual's vigilance. The Test of Variables of Attention (TOVA) and Integrated Visual and Auditory (IVA), tests are computerized go/no-go paradigms in which stimuli are presented in a series and subjects respond to target stimuli. In the TOVA test (see Forbes, *J. Clin. Psychol.* 54:461-476, 1998), the subject is instructed to respond to one tone as soon as it is heard by pressing a key and not to respond to the other tone. The IVA test (see Tinius, *Arch. Clin. Neuropsychol.* 18:439-454, 2003) uses both visual and auditory stimuli.

In another example, (see Gopher and Kahneman, *Perceptual and Motor Skills* 33:1335-1342, 1971) the auditory test involves the simultaneous presentation of different stimuli to each ear. Upon hearing an auditory cue in one ear, the subject is asked to report any subsequent number words presented to that ear, ignoring non-number words and any stimuli presented to the other ear. This test has been applied to pilots and air traffic controllers (see Boer et al., *Mil. Psychol.* 9:137-149, 1997).

Dichotic listening tests have also been used to assess hemispheric differences in language processing. In one example (Springer et al., *J. Nerv. Ment. Dis.* 179:459-467, 1991), the test consisted of precisely timed paired words presented to the right and left ears. The words were of equal duration and sound. After each presentation, subjects were asked by the examiner to identify the words or word that they heard by pointing to cards listing the stimuli used. It was found that brain-injured patients with dysphoric mood and symptoms suggestive of temporal lobe epilepsy would often recognize only one of the presented words. As in the previously described auditory test, the subject was cued to the occurrence of the stimulus.

SUMMARY OF THE INVENTION

The present invention features an auditory test that measures the subject's tendency to become distracted as indicated by a failure to recognize and report target auditory stimuli in one or both ears.

Accordingly, a first aspect of the present invention features a method of determining the attentional state of a subject that includes the steps of: a) defining target auditory stimuli consisting of number words, non-number words, or a combination thereof; b) forming an array of pairs of auditory stimuli, wherein said array comprises the target auditory stimuli and non-target stimuli; c) presenting the array as an uncued audio stream to the subject, wherein both words of each of the word pairs are presented simultaneously; d) scoring the target stimuli responded to by the subject; and e) determining the attentional state of the subject based on an evaluation of the scoring of step d). By "word" is meant any sound consisting of one or more syllables containing vowels and consonants. By "presented simultaneously" is meant any overlapping presentation of two items.

In one embodiment, the auditory stimuli include non-number words. In another embodiment, the method further includes scoring the non-target stimuli responded to by the subject in step d). Non-target stimuli can include phonetically similar words and phonetically dissimilar words, where each of the phonetically similar words sounds like one of the target stimuli and each of the phonetically dissimilar words sounds distinctly different from each of the target stimuli. In one example, the scoring of step d) includes scoring the phonetically similar words responded to by the subject. In another example, the scoring of step d) includes scoring the phonetically similar words and the phonetically dissimilar words responded to by the subject. For two words to be "phonetically similar" they both must have the same number of syllables and include similar vowel sounds for each syllable, respectively, or contain similar consonant sounds at the beginning of each syllable, respectively. An example of phonetically similar words that have the similar vowel sounds is found in the words "carry" and "hairy". Examples of phonetically similar word pairs that have similar beginning consonant sounds is found in the words "pick" and "pack" or "pick" and "pat." If two words are not phonetically similar, they are phonetically dissimilar. An example of two dissimilar words would be "pick" and "stack."

In another embodiment, the method further includes measuring the time required for the subject to respond to the target stimuli, where the determining of step e) is based on both the time required to respond and the scoring of step d).

In another embodiment, the method further includes tracking the movements of the subject, wherein the determining of step e) is based on an evaluation of the movements and the scoring of step d). Preferably the movements are tracked by a camera positioned in front of the subject. Most preferably, the movements are those of the head, leg, or foot.

The target auditory stimuli can be presented to the left and right ears of the subject. The stimuli can also be presented such that one word of the pair is presented exclusively to one ear of the subject and the other word of the pair is presented exclusively to the other ear of the subject. In this example, the auditory acuity of each ear can be assessed before word presentation and the presenting balanced accordingly. In another example, the scoring of step d) includes: i) scoring the subject's response to target stimuli presented to the right ear and, ii) scoring the subject's response to target stimuli presented to the left ear, and the determining of step e) includes comparing the scoring of step i) with the scoring of step ii).

Any of the methods of the present invention can further include simultaneously presenting to the subject a visual representation that corresponds to each of the auditory stimuli of step c), wherein the scoring of step d) is based on the subject's response to the visual representation. In one example, the subject responds to the visual representation by selecting an image presented on a monitor connected to a computer. In another example, the subject responds to the visual representation by selecting an image presented on a keyboard connected to a computer. The visual representation can be lexical or pictorial. In those embodiments of the invention in which pictorial representations are used, each symbol or picture representation is correlated to its corresponding auditory stimulus for the subject before administration of the test.

For any of the methods of the present invention each response can be stored in a computer, and the scoring of step d) and the determining of step e) performed by a computer program. In another embodiment, the subject communicates with a test administrator across a computer network.

The methods of the invention can be used to diagnose a psychological or behavioral disorder. Examples include depression, bipolar disorder, an anxiety disorder, an auditory processing disorder, petit-mal epilepsy, schizophrenia, drug addiction, an eating disorder, attention deficit disorder, attention deficit hyperactivity disorder, hyperkinetic disorder, a learning disorder, Alzheimer's disease, dementia, stroke, or traumatic brain injury. In a preferred embodiment, the disorder is attention deficit hyperactivity disorder. The methods of the invention can also be used to adjust the pharmacological treatment of a psychological or behavioral disorder. For example, the score obtained by a subject can be compared to those scores obtained from subjects diagnosed with a disorder and/or subjects not diagnosed with a disorder.

The methods of the invention can be administered to subjects that are sleep-deprived, emotionally stressed, or physically exerted, and the test results used to evaluate a subject's response to such environmental factors. The methods of the invention can also be used to evaluate the readiness of a subject for starting school or being promoted to the next grade or level. In another example, the methods of the invention can be used to determine the eligibility of a subject for obtaining a driver's license, or the suitability of a subject for a position as an air traffic controller, pilot, emergency room doctor, surgeon, police officer, military officer, or fire-fighter. The test can be administered to adolescents or post-adolescents, such as, for example, those subjects at least 12 years old, or can be designed for administration to children that are 12 years old or less.

In a related aspect, the invention features a method of determining whether a therapy affects the attentional state of a subject. This method involves making a determination of the attentional state of the subject using a method described herein before and after undergoing therapy. An altered attentional state, compared to either the attentional state of the subject when not undergoing treatment with the therapy or the attentional state of a control subject when not undergoing treatment with the therapy, indicates that the therapy affects the attentional state of the subject.

DETAILED DESCRIPTION

Attention is an important psychological ability and is involved in the ability to perform tasks accurately and quickly, to discriminate sensory stimuli, and to assimilate information appropriately. Deficits in attention have been noted in a variety of neuropsychiatric disorders, including ADHD and schizophrenia, resulting in poor task performance and difficulties with both academic and routine activities, such as operating a motorized vehicle. While there are multiple tests that involve the ability to attend to visual stimuli, a linguistic auditory continuous performance text has the capacity to detect lapses in attention and problems with selective attention.

The present invention consists of a task that requires sustained attention and the ability to attend to specific information while ignoring task-irrelevant information. In one example, a subject wears a pair of headphones that are attached to a computer and interacts with the computer through a monitor and a data input device (such as a keyboard or a mouse), each of which is linked to the computer. Auditory stimuli are stored in a digitized format in a file or set of files and software in the computer accesses the file or files and combines the words randomly or pseudo-randomly to create simultaneous word pairs. Because subjects may differ in the auditory acuity of their right and left ears, in one embodiment the computer hardware or software either assesses auditory acuity and adjusts the presentation volume accordingly, or enables the subject to adjust the volume and/or balance between the right and left headphones before the test is initiated.

During the test, a group of target stimuli are provided to the subject, followed by presenting to the subject simultaneous word pairs via headphones and visual stimuli corresponding to the auditory stimuli on the monitor screen. The auditory stream going to one ear consists of number words, while the auditory stream going to the other ear consists of non-number words. During the course of the test, the number words and non-number words can switch between ears. The auditory stream includes both target words and non-target words. Some non-target words may be phonetically dissimilar to the target is words. Other non-target words may be phonetically similar and sound like target words. Phonetically similar words can be used as a sensitive probe for false responses (errors of commission).

On the monitor screen the subject sees the number and/or non-number target words she/he is listening for. The target stimuli can be represented by words spelled out or can be represented by picture images or icons, which makes it possible to test individuals who can not read words. The subject is instructed to respond to these target stimuli as soon as they are heard by selecting words corresponding to them as they are positioned on the monitor screen (such as, for example, by locating a cursor over the screen location of the word and clicking a mouse). Alternatively, the subject is instructed to press specific keys or press specific buttons that are marked with pictorial or lexical representations of the auditory targets.

The computer then scores the target stimuli responded to by the subject. In one embodiment, the computer scores the subject's responses to the target stimuli and also assesses the latency of the response in relationship to the time of stimulus presentation. In another embodiment, the computer scores the target stimuli responded to and also scores the non-target stimuli responded to. In yet another embodiment, the computer further discriminates between the phonetically similar non-target stimuli responded to and the phonetically dissimilar non-target stimuli responded to.

The computer software can record the subject's response to each target stimulus, the rapidity of response to each target stimulus, errors of omission (failure to respond to target stimuli), errors of commission for responding to phonetically similar words, errors of commission for responding to phonetically dissimilar words, or any combination thereof. The computer can also record a subject's response to stimuli presented to the left ear and responses to stimuli presented to the right ear.

Once the responses are recorded, they are scored. The scoring can include a direct tabulation of correct and/or incorrect responses or can include weighting responses by a number of factors (e.g., by errors of omission, errors of commission, left ear responses, right ear responses, etc.). In addition, the computer can track responses over the time course of the test and weight the responses according to when they occur during the test. The attentional state of the subject is then determined based the scoring system employed.

The present invention is novel in the it is the only test of its type to assess an individual's capacity to listen for and detect one or more target words embedded in a continuous stream of verbal stimuli. This test is more cognitively challenging than other tests and provides a more meaningful assessment of a person's capacity to continuously sustain auditory attention and maintain vigilance. By using number and non-number word targets, the test provides comparative information on an individual's capacity to detect and attend to these different types of stimuli. While previously described listening tests have typically focused on hemispheric advantage for words or numbers, or on attentional capacity, methods of the present invention can measure both simultaneously. Certain task embodiments of the present invention are more demanding than those previously described in the art for dichotic listening tests in that both channels (left and right ears) can include target stimuli, possibly simultaneously. Such built in complexity makes it more difficult for a test subject to "game" the system by discerning test patterns and responding accordingly. In addition, the present invention is designed for randomized presentation of stimuli, allowing the test to be easily re-administered multiple times to the same individual.

Methods of the present invention for determining the attentional state of a subject can further include tracking the body movements of the subject. This can be accomplished by using infrared motion detection (see Teicher et al., *J. Am. Acad. Child Adolesc. Psychiatry* 35: 334-42, 1996), actigraphs (Halperin et al., *J. Am. Acad. Child Adolesc. Psychiatry* 31:190-196, 1992), or specially wired seat cushions or tilt-seats (Sprague and Sleator, *Science* 198:1274-1276, 1977). Methods that include body movement detection are particularly helpful in the assessment of ADHD, as the disorder is often characterized by hyperactivity and inattention.

One possible scenario for the use of the present invention is in the objective assessment of attentional dysfunction towards the diagnosis of ADHD or other neuropsychiatric disorders, such as schizophrenia or Alzheimer's disease; or in the assessment of an individual's functional ability to perform complex tasks, such as operating a moving vehicle. Test-retest data may be useful in providing objective evidence of medication response in ADHD or other neuropsychiatric disorders, to monitor changes in attentional ability across different time frames, to compare performance in multiple different conditions (e.g., with and without sleep deprivation), or to titrate medications for maximal efficacy. Furthermore, combining the assessment of a subject's linguistically-relevant auditory attention with the measurement of the subject's body movements markedly enhances the value of the test to detect cardinal symptoms of ADHD, and to monitor response to medications in both the attention and behavioral domains.

Other Embodiments

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each individual publication was specifically and individually indicated to be incorporated by reference.

What is claimed is:

1. A method of determining the attentional state of a subject, said method comprising using a system comprising a computer equipped with a speaker and a monitor to perform the steps of:

a) defining target auditory stimuli consisting of number words, non-number words, or a combination thereof;

b) forming an array of pairs of auditory stimuli, wherein said array comprises target stimuli and non-target stimuli, wherein said non-target stimuli comprise a plurality of phonetically similar words, each of which is phonetically similar to one of said target stimuli, and a plurality of phonetically dissimilar words, wherein each of said dissimilar words is phonetically dissimilar to each of said target stimuli;

c) presenting said array as an uncued audio stream from said speaker to said subject, wherein both words of each of said pairs are presented simultaneously, while simultaneously presenting to said subject a visual representation on said monitor corresponding to said target stimuli;

d) recording in said computer the response by said subject to said visual presentation, scoring the target stimuli responded to by said subject, scoring the non-target stimuli responded to by said subject, scoring said similar words responded to by said subject, and scoring said dissimilar words responded to by said subject, wherein said scoring is performed by a computer program; and e) on the basis of the scoring in step (d), determining the attentional state of said subject.

2. The method of claim 1, said method further comprising measuring the time required for said subject to respond to said target stimuli, wherein said determining of step e) is based on said measuring and said scoring of step d).

3. The method of claim 1, further comprising tracking the movements of said subject, wherein said determining of step e) is further based on an evaluation of said movements and said scoring of step d).

4. The method of claim 3, wherein said movements are tracked by a camera positioned in front of said subject.

5. The method of claim 3, wherein said movements are those of the head, leg, or foot of said subject.

6. The method of claim 1, wherein said target auditory stimuli are presented to the right ear and the left ear of said subject.

7. The method of claim 1, wherein said subject responds to said visual representation by selecting an image presented on said monitor.

8. The method of claim 1, wherein said subject responds to said visual representation by selecting an image presented on a keyboard connected to said computer.

9. The method of claim 1, wherein said method is used to diagnose a psychological or behavioral disorder.

10. The method of claim 9, wherein said disorder is attention deficit hyperactivity disorder.

* * * * *

UNITED STATES PATENT AND TRADEMARK OFFICE
CERTIFICATE OF CORRECTION

PATENT NO. : 8,430,672 B2  
APPLICATION NO. : 11/660880  
DATED : April 30, 2013  
INVENTOR(S) : Martin H. Teicher et al.

Page 1 of 1

It is certified that error appears in the above-identified patent and that said Letters Patent is hereby corrected as shown below:

In the Specifications:

Column 4, Line 38, replace "target is words." with --target words.--.

Signed and Sealed this
Twentieth Day of August, 2013

Teresa Stanek Rea
*Acting Director of the United States Patent and Trademark Office*